United States Patent
Mori et al.

(10) Patent No.: US 10,259,149 B2
(45) Date of Patent: Apr. 16, 2019

(54) STRUCTURE, PRODUCTION METHOD THEREOF, AND ARTICLE PROVIDED WITH SAID STRUCTURE

(71) Applicant: Mitsubishi Rayon Co., Ltd., Chiyoda-ku (JP)

(72) Inventors: Seiichiro Mori, Toyohashi (JP); Kousuke Fujiyama, Otake (JP); Go Otani, Otake (JP); Yusuke Nakai, Otake (JP); Tetsuya Jigami, Otake (JP)

(73) Assignee: Mitsubishi Chemical Corporation, Tokyo (JP)

( * ) Notice: Subject to any disclaimer, the term of this patent is extended or adjusted under 35 U.S.C. 154(b) by 182 days.

(21) Appl. No.: 15/021,745

(22) PCT Filed: Sep. 18, 2014

(86) PCT No.: PCT/JP2014/074662
§ 371 (c)(1),
(2) Date: Mar. 14, 2016

(87) PCT Pub. No.: WO2015/041283
PCT Pub. Date: Mar. 26, 2015

(65) Prior Publication Data
US 2016/0229095 A1    Aug. 11, 2016

(30) Foreign Application Priority Data
Sep. 18, 2013 (JP) .................................. 2013-193215

(51) Int. Cl.
*B29C 35/08* (2006.01)
*G02B 1/11* (2015.01)
(Continued)

(52) U.S. Cl.
CPC .............. *B29C 43/58* (2013.01); *B22C 9/061* (2013.01); *B29C 35/0805* (2013.01); *B32B 3/30* (2013.01);
(Continued)

(58) Field of Classification Search
CPC ....... B29C 43/58; B29C 43/222; B29C 43/46; B29C 2035/0827; B29C 2043/463;
(Continued)

(56) References Cited

U.S. PATENT DOCUMENTS

2009/0246494 A1* 10/2009 Matsumoto .......... B29C 43/222
428/220
2010/0177397 A1* 7/2010 Kamiyama .............. G02B 5/02
359/609
(Continued)

FOREIGN PATENT DOCUMENTS

JP    2009-031764 A    2/2009
JP    2012-163723 A    8/2012
(Continued)

OTHER PUBLICATIONS

Okamoto, 2009, JP 2009031764 A, (Google English Translation downloaded on Dec. 20, 2017).*
(Continued)

*Primary Examiner* — Nathan L Van Sell
(74) *Attorney, Agent, or Firm* — Morgan, Lewis & Bockius LLP

(57) ABSTRACT

A structure with a substrate, and a fine-unevenness-structure layer provided to at least one surface of the substrate, wherein the fine-unevenness-structure layer is disposed at a surface of the structure, the indentation elastic modulus of the structure is 1-1300 MPa, and the ratio (Δμ) of the rate of change of the coefficient of kinetic friction of the surface of the structure is 0.15-1.05, wherein Δμ=Δμf/Δμs: Δμs repre-
(Continued)

sents the rate of change of the coefficient of kinetic friction of the surface of the structure at an initial-abrasion stage of a reciprocating abrasion test; and $\Delta\mu f$ represents the rate of change of the coefficient of kinetic friction of the surface of the structure immediately prior to the end of the reciprocating abrasion test. This structure exhibits excellent scratch resistance without compromising on the optical performance thereof, such as the antireflection performance.

14 Claims, 4 Drawing Sheets

(51) Int. Cl.

| | |
|---|---|
| *G02B 1/118* | (2015.01) |
| *B32B 3/30* | (2006.01) |
| *B32B 27/30* | (2006.01) |
| *B32B 27/06* | (2006.01) |
| *B29C 59/04* | (2006.01) |
| *B29C 43/22* | (2006.01) |
| *B29C 43/46* | (2006.01) |
| *B29L 11/00* | (2006.01) |
| *B29L 7/00* | (2006.01) |
| *B29K 105/00* | (2006.01) |
| *B29C 43/58* | (2006.01) |
| *B22C 9/06* | (2006.01) |
| *C25D 11/12* | (2006.01) |
| *C25D 11/16* | (2006.01) |
| *G01N 3/56* | (2006.01) |

(52) U.S. Cl.
CPC ............ *B32B 27/06* (2013.01); *B32B 27/308* (2013.01); *C25D 11/12* (2013.01); *C25D 11/16* (2013.01); *G01N 3/56* (2013.01); *G02B 1/11* (2013.01); *G02B 1/118* (2013.01); *B29C 43/222* (2013.01); *B29C 43/46* (2013.01); *B29C 59/046* (2013.01); *B29C 2035/0827* (2013.01); *B29C 2043/463* (2013.01); *B29C 2043/467* (2013.01); *B29K 2105/0002* (2013.01); *B29K 2995/0093* (2013.01); *B29L 2007/001* (2013.01); *B29L 2011/00* (2013.01); *B32B 2307/102* (2013.01); *B32B 2307/304* (2013.01); *B32B 2307/51* (2013.01); *B32B 2419/00* (2013.01); *B32B 2439/00* (2013.01); *B32B 2551/00* (2013.01)

(58) Field of Classification Search
CPC .......... B29C 2043/467; B29C 35/0805; B29C 59/046; B22C 9/061; C25C 11/12; C25D 11/16; C25D 11/12; G01N 3/56; G02B 1/11; G02B 1/118; B29L 2011/00; B29L 2007/001; B29K 2105/0002; B29K 2995/0093; B32B 3/30; B32B 27/308; B32B 27/06; B32B 2307/304; B32B 2307/51; B32B 2419/00; B32B 2439/00; B32B 2551/00; B32B 2307/102
See application file for complete search history.

(56) References Cited

U.S. PATENT DOCUMENTS

| | | | |
|---|---|---|---|
| 2010/0243458 A1* | 9/2010 | Kojima | B29C 33/38 |
| | | | 205/50 |
| 2010/0323165 A1* | 12/2010 | Sakuma | G02B 1/118 |
| | | | 428/167 |
| 2011/0157704 A1* | 6/2011 | Sato | B29C 33/38 |
| | | | 359/601 |
| 2013/0075962 A1* | 3/2013 | Jigami | B29C 33/62 |
| | | | 264/496 |
| 2013/0296456 A1 | 11/2013 | Kobayashi et al. | |

FOREIGN PATENT DOCUMENTS

| | | |
|---|---|---|
| JP | 2013-039711 A | 2/2013 |
| WO | 2011/155499 A1 | 12/2011 |
| WO | 2012/099164 A1 | 7/2012 |

OTHER PUBLICATIONS

International Search Report dated Dec. 16, 2014 for International application No. PCT/JP2014/074662.

\* cited by examiner

STRUCTURE, PRODUCTION METHOD THEREOF, AND ARTICLE PROVIDED WITH SAID STRUCTURE

TECHNICAL FIELD

The present invention relates to a structure, a production method thereof, and an article provided with the structure. Priority is claimed on Japanese Patent Application No. 2013-193215 filed in Japan on Sep. 18, 2013, the content of which is incorporated herein by reference.

BACKGROUND ART

A structure having a fine concavo-convex structure on the surface is known to exhibit antireflection performance based on a continuous change in the refractive index. Furthermore, a fine concavo-convex structure is also capable of exhibiting super-water-repellent performance as a result of the lotus effect.

In order for a fine concavo-convex structure to exhibit satisfactory antireflection performance, the interval between adjoining convexities or concavities needs to be smaller than or equal to the wavelength of visible light. Regarding the method for producing a structure having such a fine concavo-convex structure on the surface, for example, a so-called nanoimprint method including the following steps (i) to (iii) is known:

(i) a step of interposing an active energy ray-curable resin composition between a substrate and a mold having a reverse structure of a fine concavo-convex structure on the surface;

(ii) a step of irradiating the active energy ray-curable resin composition with active energy rays such as ultraviolet radiation, and thereby curing the active energy ray-curable resin composition; and (iii) a step of separating the cured product and the mold.

However, a structure having a fine concavo-convex structure on the surface has poor scratch resistance compared to a structure having a hard coat layer with a smooth surface, which has been produced from the same material as the material forming the fine concavo-convex structure. Thus, such a structure having a fine concavo-convex structure on the surface has a problem that the antireflection performance is easily deteriorated because the protrusions having a size in the order of nanometers are susceptible to damage, or because the protrusions wear out when the operation of wiping off the dirt adhered to the surface is repeatedly conducted.

Regarding the method of enhancing the scratch resistance of a structure having a fine concavo-convex structure on the surface, a method of incorporating a lubricating agent into the material that forms the fine concavo-convex structure to make the surface slippery, and thereby preventing the protrusions having a size in the order of nanometers from being damaged, may be mentioned.

However, lubricating agents often bleed out to the structure surfaces, and thereby cause a problem that the reflectance of the surface or the haze value is increased, and the antireflection performance is deteriorated.

Furthermore, a method of imparting resilience to the protrusions having a size in the order of nanometers by using a flexible resin composition for the formation of the fine concavo-convex structure, and turning aside any burden, has also been suggested (Patent Document 1).

However, as in the case of Patent Document 1, when resilience is imparted to the protrusions having a size in the order of nanometers, the surface is prone to become sticky so that the friction force is increased, and strong force is required to wipe off dirt. Furthermore, when dirt is wiped off with strong force, the protrusions having a size in the order of nanometers are easily damaged, and cause a problem that leads to deterioration of the antireflection performance.

CITATION LIST

Patent Document

Patent Document 1: JP 2012-163723 A

SUMMARY OF THE INVENTION

Problem to be Solved by the Invention

The invention was achieved in view of the circumstances described above, and it is an object of the invention to provide a structure having excellent antireflection performance and scratch resistance, and a method for producing a structure having excellent antireflection performance and scratch resistance.

Means for Solving Problem

The present inventors paid attention to the changes in scratch resistance and the coefficient of kinetic friction and conducted a thorough investigation. As a result, the present inventors found that as the stage of initial wear is maintained longer in a reciprocating abrasion test, a structure has superior scratch resistance. Then, the present inventors found that when the elastic modulus of the material that forms a fine concavo-convex structure is controlled, and the increase in the coefficient of kinetic friction occurring when a reciprocating abrasion test is performed on a face having the fine concavo-convex structure, is suppressed to be within a predetermined range, a structure having excellent scratch resistance can be obtained without impairing the optical performance such as antireflection performance. Thus, the present inventors completed the invention.

That is, the invention includes the following embodiments.

[1] A structure having a substrate; and a fine concavo-convex structure layer provided on at least one face of the substrate, the fine concavo-convex structure being disposed on the surface of the structure, and the structure having an indentation modulus of 1 MPa to 1300 MPa, and has a ratio of the rates of change ($\Delta\mu$) in the coefficient of kinetic friction of the surface of the structure, which is represented by the following Formula (1), of 0.15 to 1.05:

$$\Delta\mu = \Delta\mu f / \Delta\mu s \qquad (1)$$

wherein in Formula (1), $\Delta\mu s$ represents the rate of change in the coefficient of kinetic friction in the stage of initial wear in a reciprocating abrasion test for the surface of the structure; and $\Delta\mu f$ represents the rate of change in the coefficient of kinetic friction immediately before the end of the test in the reciprocating abrasion test for the surface of the structure.

[2] The structure according to [1], wherein the average interval between adjoining convexities in the fine concavo-convex structure layer is 400 nm or less, and the aspect ratio of the convexities is 0.7 to 1.4.

[3] The structure according to [1], wherein the average interval between adjoining convexities in the fine concavo-convex structure layer is 120 nm to 250 nm.

[4] The structure according to any one of [1] to [3], wherein the fine concavo-convex structure layer contains a cured product of an active energy ray-curable resin composition, and the active energy ray-curable resin composition includes at least a (meth)acrylate having an oxyethylene group.

[5] The structure according to any one of [1] to [4], wherein the ratio of the rates of change in the coefficient of kinetic friction of the structure surface, which is represented by Formula (1) described above, is 0.3 to 1.0.

[6] The structure according to any one of [1] to [5], wherein the ratio of the rates of change in the coefficient of kinetic friction of the structure surface, which is represented by Formula (1), is 0.6 to 0.9.

[7] The structure according to any one of [1] to [6], wherein the coefficient of kinetic friction of the structure surface is 0.55 or less.

[8] The structure according to any one of [1] to [7], wherein the coefficient of kinetic friction of the structure surface is 0.38 to 0.5.

[9] The structure according to any one of [1] to [8], wherein the indentation modulus of the structure is 160 MPa to 300 MPa.

[10] The structure according to any one of [1] to [9], further including an intermediate layer between the substrate and the fine concavo-convex structure layer.

[11] The structure according to [10], wherein the intermediate layer contains a cured product of the active energy ray-curable resin composition, and the active energy ray-curable resin composition includes at least one (meth)acrylate selected from the group consisting of an ester (meth)acrylate and a urethane (meth)acrylate.

[12] The structure according to any one of [1] to [11], wherein the substrate is a light-transmitting substrate.

[13] An article provided with the structure according to any one of [1] to [12].

[14] A method for producing the structure according to any one of [1] to [12], the method including a step of forming a fine concavo-convex structure layer by a nanoimprint method.

Effect of the Invention

The invention can provide a structure having excellent scratch resistance without impairing optical performance such as antireflection performance, a method for producing the structure, and an article provided with the structure.

MODE(S) FOR CARRYING OUT THE INVENTION

Hereinafter, the invention will be described in detail.

Meanwhile, according to the present specification, the term "surface layer" means the fine concavo-convex structure layer disposed on the surface of the structure.

Furthermore, the "active energy rays" according to the present specification means visible light, ultraviolet radiation, an electron beam, plasma, heat rays (infrared radiation), or the like.

Furthermore, "(meth)acrylate" according to the present specification is a generic name for acrylate and methacrylate, and "(meth)acrylic acid" is a generic name for acrylic acid and methacrylic acid. "(Meth)acrylonitrile" is a generic name for acrylonitrile and methacrylonitrile, and "(meth)acrylamide" is a generic name for acrylamide and methacrylamide.

Figure 1:
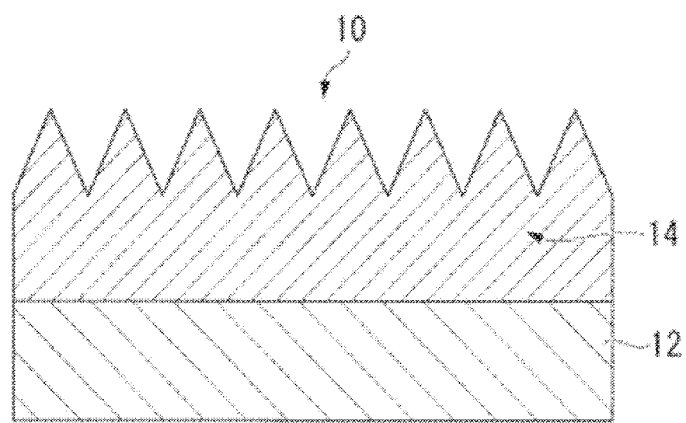
FIG. 1 is a cross-sectional view diagram illustrating an example of the structure of the invention.

In FIG. 1, different scales are used in order to adjust the various layers to sizes of the extent that can be recognized in the diagram.

Figure 2:
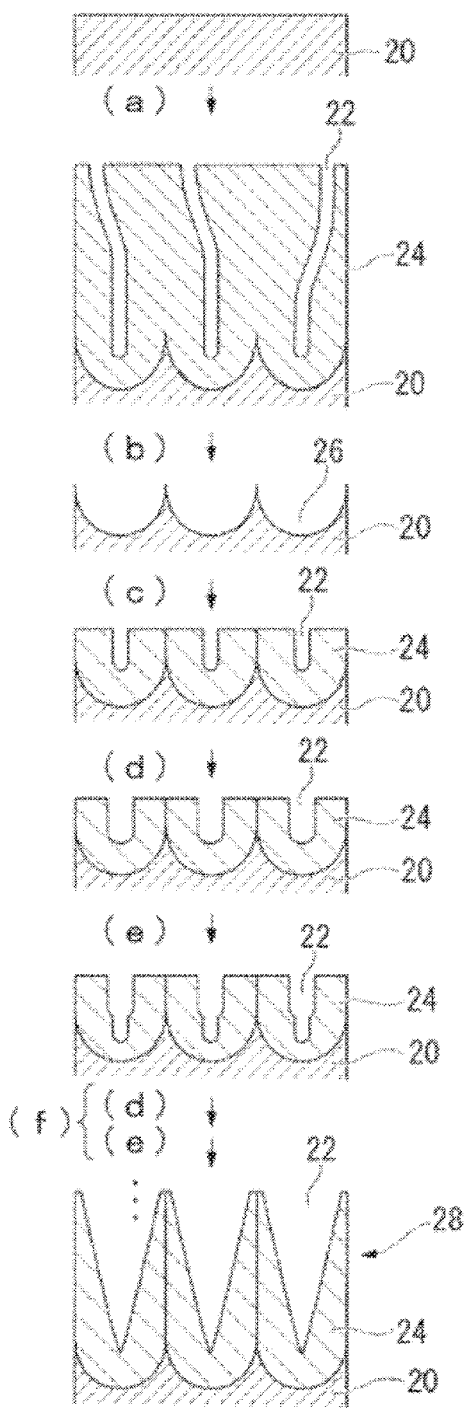
FIG. 2 is a cross-sectional view diagram illustrating a production process for a mold having anodized alumina on the surface.
Figure 3:
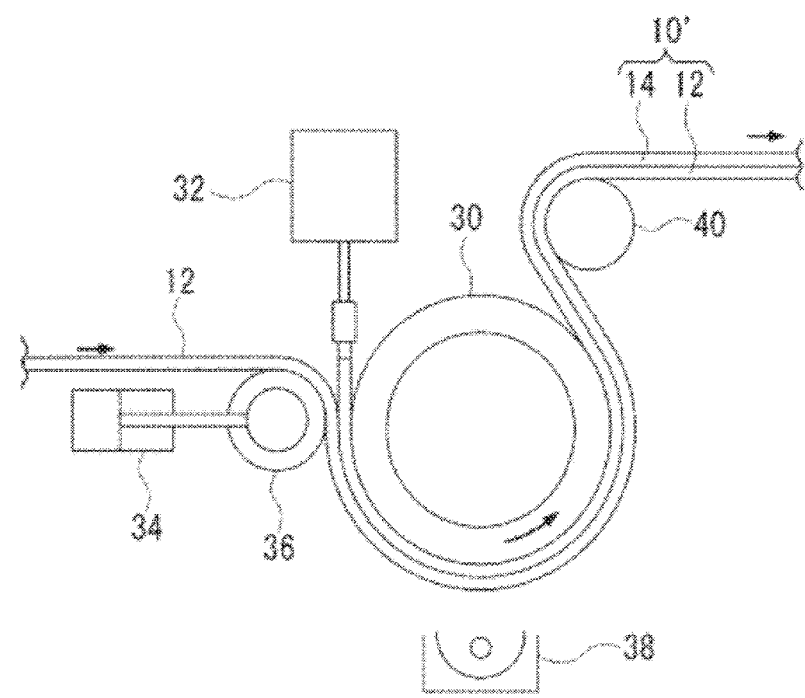
FIG. 3 is a configuration diagram illustrating an example of a production apparatus for the structure of the invention.

Furthermore, in FIG. 2 and FIG. 3, the same symbols may be assigned to the same constitutional elements in FIG. 1, and descriptions thereof may not be repeated.

<Structure>

The structure of the invention has a substrate, and a fine concavo-convex structure layer provided on at least one face of the substrate.

It is desirable that the fine concavo-convex structure layer is disposed on at least surface of the structure, and may also be disposed on both surfaces. As will be described below, when the fine concavo-convex structure is provided on the surface of the structure, the structure may have excellent antireflection performance.

FIG. 1 is a cross-sectional view diagram illustrating an example of the structure of the invention. The structure 10 is configured to include a fine concavo-convex structure layer 14 laminated on a substrate 12, and the fine concavo-convex structure layer 14 has a fine concavo-convex structure on the surface opposite to the face that is in contact with the substrate.

The structure of the invention has an indentation modulus of 1 MPa to 1300 MPa. Furthermore, the ratio of the rates of change ($\Delta\mu$) in the coefficient of kinetic friction of the structure surface represented by the following Formula (1) is 0.15 to 1.05.

$$\Delta\mu = \Delta\mu f / \Delta\mu s \quad (1)$$

wherein in Formula (1), $\Delta\mu s$ represents the rate of change in the coefficient of kinetic friction in the stage of initial wear in a reciprocating abrasion test of the structure surface; and $\Delta\mu f$ represents the rate of change in the coefficient of kinetic friction immediately before the end of the test in the reciprocating abrasion test of the structure surface.

Thereby, the structure of the invention is characterized by having excellent scratch resistance performance.

"Fine Concavo-Convex Structure Layer"

The fine concavo-convex structure layer is a layer having a fine concavo-convex structure on at least one surface.

The shape of the concavities and convexities of the fine concavo-convex structure is not particularly limited as long as the effects of the invention are obtained; however, a so-called moth eye structure or an inverse structure thereof, in which a plural number of protrusions (convexities) having an approximately conical shape, a pyramidal shape or the like are aligned, is preferred. Particularly, in the case of a moth eye structure in which the average interval between adjoining convexities is less than or equal to the wavelength of visible light (400 nm), since the refractive index increases continuously from the refractive index of air to the refractive index of the material, the structure is effective as a means for antireflection.

The average interval between adjoining convexities (hereinafter, may be referred to as the "pitch of convexities") in the fine concavo-convex structure is preferably less than or equal to the wavelength of visible light, that is, 400 nm or less. When the pitch of the convexities is 400 nm or less, the reflectance is low, and the wavelength-dependency of the reflectance is low. The pitch of the convexities is more preferably 120 nm to 380 nm, even more preferably 140 nm to 260 nm, and most preferably 160 nm to 200 nm, from the viewpoint that the convexity structure can be easily formed.

Meanwhile, the average interval between adjoining convexities can be calculated by observing a cross-sectional view of the structure of the invention using an electron microscope, measuring the interval between adjoining convexities (distance from the center of a convexity to the center of an adjacent convexity) at 50 sites, and averaging these values.

The average height of the convexities of the fine concavo-convex structure layer is preferably 100 nm to 300 nm, more preferably 120 nm to 250 nm, particularly preferably 150 nm to 220 nm, and most preferably 160 nm to 190 nm. When the average height of the convexities is 100 nm or more, the reflectance is low, and the wavelength-dependency of the reflectance is low. Furthermore, when the average height of the convexities is 300 nm or less, the phenomenon in which the convexities are brought into contact and integrated can be easily suppressed, which is preferable. Meanwhile, the average height of the convexities can be calculated by measuring, at 50 sites, the distance between the apex of a convexity and the bottommost part of a concavity existing between convexities, which is obtainable when a cross-sectional view of the structure is observed at a magnification ratio of 30,000 times using the electron microscope described above, and averaging these values.

Furthermore, the aspect ratio of the convexities (average height of the convexities/average interval between adjoining convexities) is preferably 0.8 to 5, more preferably 0.7 to 1.4, and even more preferably 0.8 to 1.2. When the aspect ratio of the convexities is 0.8 or more, the reflectance is sufficiently lowered. When the aspect ratio of the convexities is 5 or less, satisfactory scratch resistance of the convexities is obtained.

"Substrate"

The substrate is a support that supports the fine concavo-convex structure layer. The shape can be appropriately selected, and the shape may be a sheet form or may be a film form. Here, a sheet form means a product having a thickness of more than 200 μm, and a film form means a product having a thickness of 200 μm or less. Also, the substrate may be an injection molded product, may be an extrusion molded product, or may be a cast molded product.

Examples of the material for the substrate include an acrylic resin (polymethyl methacrylate or the like), a polycarbonate, a styrene (co)polymer, a methyl methacrylate-styrene copolymer, cellulose diacetate, cellulose triacetate, cellulose acetate butyrate, a polyester (polyethylene terephthalate or the like), a polyamide, a polyimide, a polyether sulfone, a polysulfone, a polyolefin (polyethylene, polypropylene, or the like), polymethylpentene, polyvinyl chloride, polyvinyl acetal, polyether ketone, polyurethane, and glass. These materials may be used singly, or two or more kinds thereof may be used in combination.

The surface of the substrate may be subjected to a coating treatment, a corona treatment or the like, in order to improve adhesiveness, antistatic properties, scratch resistance, weather resistance, and the like.

The substrate used for the structure of the invention is preferably a light-transmitting substrate that transmits light. When the substrate is capable of transmitting light, an article having excellent light transmissibility and antireflection performance is obtained. Also, in a case in which a fine concavo-convex structure is formed using a mold that does not readily transmit light, the structure can be irradiated with active energy rays through the substrate side.

Examples of such a light-transmitting substrate include substrates formed from materials such as an acrylic resin, a polycarbonate, cellulose triacetate, a polyester, a polyolefin, and glass. These materials may be used singly, or two or more kinds thereof may be used in combination. Furthermore, a substrate formed from such a material is preferable because the substrate has light transmitting properties. That is, the substrate of the invention is preferably a light-transmitting substrate.

The term "light-transmitting" according to the invention means a substrate that transmits visible light. The transmittance for visible light of the light-transmitting substrate is preferably 85% or higher.

Furthermore, the thickness of the substrate is preferably 1 μm to 10,000 μm, and more preferably 15 μm to 200 μm. Also, the thickness of the substrate can be measured using a micrometer.

"Material for Forming Fine Concavo-Convex Structure Layer"

Examples of the material for forming a fine concavo-convex structure layer include an active energy ray-curable resin composition, a thermoplastic resin, and an inorganic material. From the viewpoint of the ease of forming a fine concavo-convex structure, the material is preferably an active energy ray-curable resin composition.

Hereinafter, the active energy ray-curable resin composition will be described in detail.

<Active Energy Ray-Curable Resin Composition>

The active energy ray-curable resin composition (hereinafter, may be simply referred to as "resin composition") is a resin composition including a polymerizable component which undergoes a polymerization reaction when irradiated with active energy rays, and is cured.

The polymerizable component is a component which appropriately includes, for example, a monomer, an oligomer, or a reactive polymer, all of which have a radical polymerizable bond and/or a cationically polymerizable bond in the molecule. Furthermore, the resin composition usually includes a polymerization initiator for curing the polymerizable component.

(Polymerizable Component)

Examples of the monomer having a radical polymerizable bond in the molecule include monofunctional monomers such as (meth)acrylates (methyl (meth)acrylate, ethyl (meth)acrylate, propyl (meth)acrylate, n-butyl (meth)acrylate, i-butyl (meth)acrylate, s-butyl (meth)acrylate, tert-butyl (meth)acrylate, 2-ethylhexyl (meth)acrylate, lauryl (meth)acrylate, an alkyl (meth)acrylate, tridecyl (meth)acrylate, stearyl (meth)acrylate, cyclohexyl (meth)acrylate, benzyl (meth)acrylate, phenoxyethyl (meth)acrylate, isobornyl (meth)acrylate, glycidyl (meth)acrylate, tetrahydrofurfuryl (meth)acrylate, allyl (meth)acrylate, 2-hydroxyethyl (meth)acrylate, hydroxypropyl (meth)acrylate, 2-methoxyethyl (meth)acrylate, 2-ethoxyethyl (meth)acrylate, and the like), (meth)acrylic acid, (meth)acrylonitrile, styrenes (styrene, α-methylstyrene, and the like), and (meth)acrylamides ((meth)acrylamide, N-dimethyl (meth)acrylamide, N-diethyl (meth)acrylamide, dimethylaminopropyl (meth)acrylamide, and the like); bifunctional monomers such as ethylene glycol di(meth)acrylate, tripropylene glycol di(meth)acrylate, ethylene oxide isocyanurate-modified di(meth)acrylate, triethylene glycol di(meth)acrylate, diethylene glycol di(meth)acrylate, polyethylene glycol di(meth)acrylate, neopentyl glycol di(meth)acrylate, 1,6-hexanediol di(meth)acrylate, 1,5-pentanediol di(meth)acrylate, 1,3-butylene glycol di(meth)acrylate, polybutylene glycol di(meth)acrylate, 2,2-bis(4-(meth)acryloxypolyethoxyphenyl)propane, 2,2-bis(4-(meth)acryloxyethoxyphenyl)propane, 2,2-bis(4-(3-(meth)acryloxy-2-hydroxypropoxy)phenyl)propane, 1,2-bis(3-(meth)acryloxy-2-hydroxypropoxy)ethane, 1,4-bis(3-(meth)acryloxy-2-hydroxypropoxy)butane, dimethyloltricyclodecane di(meth)acrylate, di(meth)acrylate of bisphenol A ethylene oxide adduct, di(meth)acrylate of bisphenol A propylene oxide adduct, di(meth)acrylate of neopentyl glycol hydroxypivalate, divinylbenzene, and methylenebisacrylamide; trifunctional monomers such as pentaerythritol tri(meth)acrylate, trimethylolpropane tri(meth)acrylate, trimethylolpropane ethylene oxide-modified tri(meth)acrylate, trimethylolpropane propylene oxide-modified triacrylate, trimethylolpropane ethylene oxide-modified triacrylate, ethylene oxide isocyanurate-modified tri(meth)acrylate, and glycerin ethylene oxide-modified triacrylate; polyfunctional monomers such as condensation reaction mixtures of succinic acid/trimethylolethane/acrylic acid, ethoxylated pentaerythritol tetra(meth)acrylate, dipentaerythritol hexa(meth)acrylate, dipentaerythritol penta(meth)acrylate, ditrimethylolpropane tetraacrylate, tetramethylolmethane tetra(meth)acrylate, and polyglycerin polyacrylate, and ethylene oxide adducts or propylene oxide adducts of these polyfunctional monomers; bifunctional or higher-functional urethane acrylates, bifunctional or higher functional polyester acrylates, and bifunctional or higher-functional silicone (meth)acrylate. These may be used singly, or in combination of two or more kinds thereof.

Examples of the oligomer and the reactive polymer, both having radical polymerizable bonds in the molecule, include unsaturated polyesters (a condensation product between an unsaturated dicarboxylic acid and a polyhydric alcohol, and the like), polyester (meth)acrylate, polyether (meth)acrylate, polyether (meth)acrylate, polyol (meth)acrylate, epoxy (meth)acrylate, urethane (meth)acrylate, cationic polymerization type epoxy compounds, and homopolymers or copolymers of the above-mentioned monomers having radical polymerizable bonds in side chains.

The monomer, oligomer or reactive polymer having cationically polymerizable bonds in the molecule may be ay compound having a cationically polymerizable functional group (cationically polymerizable compound), and may be any of a monomer, an oligomer, or a prepolymer.

Examples of the cationically polymerizable functional group include, as functional groups having high practical usability, cyclic ether groups (an epoxy group, an oxetanyl group, an oxazolyl group, and the like), a vinyloxy group, a vinyl ether group, and a carbonate group (O—CO—O group).

Examples of the cationically polymerizable compound include cyclic ether compounds (an epoxy compound, an oxetane compound, and the like), vinyl ether compounds, and carbonate-based compounds (a cyclic carbonate compound, a dithiocarbonate compound, and the like).

Specific examples of the monomer having a cationically polymerizable bond in the molecule include the aforementioned monomers having an epoxy group, an oxetanyl group, an oxazolyl group, a vinyloxy group, a vinyl ether group, a carbonate group, and the like, and among these, a monomer having an epoxy group is particularly preferred. Specific examples of the oligomer and reactive polymer having cationically polymerizable bonds include cationic polymerization type epoxy compounds. Examples of commercially available products of the cationic polymerization type epoxy compounds include "DENACOL" series manufactured by Nagase ChemteX Corp.; "EPOLIGHT" series manufactured by Kyoeisha Chemical Co., Ltd.; "ADEKA RESIN" series and "ADEKA GLYCIROL" manufactured by Adeka Corp.

According to an embodiment of the invention, it is preferable that the fine concavo-convex structure layer contains a cured product of an active energy ray-curable resin composition, and the active energy ray-curable resin composition includes at least a (meth)acrylate having an oxyethylene group. Furthermore, it is preferable that the (meth)acrylate having an oxyethylene group is at least one selected from the group consisting of polyethylene glycol diacrylate, an ethylene oxide adduct of dipentaerythritol hexaacrylate, ethoxylated pentaerythritol tetraacrylate, trimethylolpropane ethylene oxide-modified triacrylate, ethylene oxide isocyanurate-modified triacrylate, glycerin ethylene oxide-modified triacrylate, and polyglycerin ethylene oxide-modified polyacrylate.

The content of the (meth)acrylate having an oxyethylene group is preferably 30 parts to 100 parts by mass, more preferably 30 parts to 80 parts by mass, and particularly preferably 30 parts to 70 parts by mass, relative to 100 parts by mass of the polymerizable components in the active energy ray-curable resin composition.

When the material that forms the fine concavo-convex structure layer contains a (meth)acrylate having an oxyethylene group, a structure having excellent scratch resistance can be obtained.

(Polymerization Initiator)

Regarding the polymerization initiator, known compounds may be used.

In a case in which the resin composition is cured by utilizing a photoreaction of visible light, ultraviolet radiation or the like, examples of the photopolymerization initiator include a radical polymerization initiator and a cationically polymerization initiator.

The radical polymerization initiator may be any compound which generates a radical when irradiated with known active energy rays, and examples thereof include an acetophenone-based photopolymerization initiator, a benzoin-based photopolymerization initiator, a benzophenone-based photopolymerization initiator, a thioxanthone-based photopolymerization initiator, and an acylphosphine oxide-based photopolymerization initiator. These radical polymerization initiators may be used singly or in combination of two or more kinds thereof. In the case of using the radical polymerization initiators in combination, it is preferable to use two or more kinds having different absorption wavelengths in combination.

Examples of the acetophenone-based photopolymerization initiator include acetophenone, p-(tert-butyl)-1',1',1'-trichloroacetophenone, chloroacetophenone, 2',2'-diethoxyacetophenone, hydroxyacetophenone, 2,2-dimethoxy-2'-phenylacetophenone, 2-aminoacetophenone, 2-hydroxy-2-methyl-1-phenylpropan-1-one, benzyl dimethyl ketal, 1-hydroxycyclohexyl phenyl ketone, 1-[4-(2-hydroxyethoxy)-phenyl]-2-hydroxy-2-methyl-1-propan-1-one, 2-hydroxy-1-{4-[4-(2-hydroxy-2-methylpropionyl)-benzyl]phenyl}-2-methylpropan-1-one, 2-methyl-2-morpholino(4-thiomethylphenyl)propan-1-one, 2-benzyl-2-dimethylamino-1-(4-morpholinophenyl)-butanone, and 2-(dimethylamino)-2-[(4-methylphenyl)methyl]-1-[4-(4-morpholinyl)phenyl]-1-butanone.

Examples of the benzoin-based photopolymerization initiator include benzil, benzoin, benzoin methyl ether, benzoin ethyl ether, benzoin isopropyl ether, and benzoin isobutyl ether.

Examples of the benzophenone-based photopolymerization initiator include benzophenone, benzoylbenzoic acid, methyl benzoylbenzoate, methyl-o-benzoylbenzoate, 2,4,6-trimethylbenzophenone, 4-phenylbenzophenone, hydroxybenzophenone, hydroxypropylbenzophenone, acrylbenzophenone, 4,4'-bis(dimethylamino)benzophenone, and 4,4-bis(diethylamino)benzophenone.

Examples of the thioxanthone-based photopolymerization initiator include thioxanthone, 2-chlorothioxanthone, 2,4-dichlorothioxanthone, 2-methylthioxanthone, isopropylthioxanthone, diethylthioxanthone, and dimethylthioxanthone.

Examples of the acylphosphine oxide-based photopolymerization initiator include 2,4,6-trimethylbenzoyldiphenylphosphine oxide, bis(2,6-dimethoxybenzoyl)-2,4,4-trimethylpentylphosphine oxide, benzoyldiethoxyphosphine oxide, and bis(2,4,6-trimethylbenzoyl)phenylphosphine oxide.

Examples of other radical polymerization initiators include α-acyloxime ester, benzyl-(o-ethoxycarbonyl)-α-monooxime, glyoxyester, 3-keto coumarin, 2-ethylanthraquinone, camphor-quinone, tetramethylthiuram sulfide, azobisisobutyronitrile, benzoyl peroxide, dialkyl peroxide, and tert-butyl peroxypivalate.

The cationic polymerization initiator may be any compound which generates an acid when irradiated with known active energy rays, and examples thereof include a sulfonium salt, an iodonium salt, and a phosphonium salt. These cationic polymerization initiators may be used singly or in combination of two or more kinds thereof.

Examples of the sulfonium salt include triphenylsulfonium hexafluorophosphate, triphenylsulfonium hexafluoroantimonate, bis(4-(diphenylsulfonio)-phenyl) sulfide-bis(hexafluorophosphate), 4-di(p-toluyl)sulfonio-4'-tert-butylphenylcarbonyl diphenyl sulfide hexafluoroantimonate, 7-di(p-toluyl)sulfonio-2-isopropylthioxanthone hexafluorophosphate, and 7-di(p-toluyl)sulfonio-2-isopropylthioxanthone hexafluoroantimonate.

Examples of the iodonium salt include diphenyliodonium hexafluorophosphate, diphenyliodonium hexafluoroantimonate, bis(dodecylphenyl)iodonium tetrakis(pentafluorophenyl)borate.

Examples of the phosphonium salt include tetrafluorophosphonium hexafluorophosphate and tetrafluorophosphonium hexafluoroantimonate.

Regarding these photopolymerization initiators, from the viewpoint that a structure which satisfies the indentation modulus and Δμ described above can be easily obtained, at least one photopolymerization initiator selected from the group consisting of an acetophenone-based photopolymerization initiator and an acylphosphine oxide-based photopolymerization initiator is preferred.

In a case in which the resin composition is cured by utilizing a thermal reaction of infrared radiation or the like, examples of the thermal polymerization initiator include organic peroxides (methyl ethyl ketone peroxide, benzoyl peroxide, dicumyl peroxide, tert-butyl hydroperoxide, cumene hydroperoxide, tert-butyl peroxyoctoate, tert-butyl peroxybenzoate, lauroyl peroxide, and the like), azo-based compounds (azobisisobutyronitrile and the like), and redox polymerization initiators obtained by combining amines (N,N-dimethylaniline, N,N-dimethyl-p-toluidine, and the like) to the organic peroxides described above.

These thermal polymerization initiators may be used singly or in combination of two or more kinds thereof.

The content of the polymerization initiator is preferably 0.1 parts to 10 parts by mass relative to 100 parts by mass of the polymerizable components. When the content of the polymerization initiator is 0.1 parts by mass or more, polymerization can easily proceed. When the content of the polymerization initiator is 10 parts by mass or less, there is less chance that the cured product thus obtainable is colored, or that the mechanical strength is decreased.

(Other Components)

The resin composition may also include a non-reactive polymer.

Examples of the non-reactive polymer include an acrylic resin, a styrene-based resin, a polyurethane resin, a cellulose resin, a polyvinyl butyral resin, a polyester resin, a thermoplastic elastomer, and a modified silicone resin. Among these, from the viewpoint of enhancing the scratch resistance of the structure, it is preferable that the resin composition includes a modified silicone resin. Furthermore, in a case in which the resin composition includes a modified silicone resin, the content of the resin is preferably 1 part to 13 parts by mass, more preferably 1 part to 9 parts by mass, and particularly preferably 5 parts to 9 parts by mass, relative to 100 parts by mass of the polymerizable components.

Furthermore, the resin composition may also include, if necessary, known additives such as a surfactant, a mold release agent, a lubricating agent, a plasticizer, an antistatic agent, a photostabilizer, an oxidation inhibitor, a flame retardant, a flame retardant aid, a polymerization inhibitor, a filler, a silane coupling agent, a colorant, a reinforcing agent, an inorganic filler, inorganic or organic fine particles, an impact resistance modifier, and a small amount of a solvent, in addition to the components described above.

(Viscosity)

Regarding the viscosity of the resin composition, the details will be described below, but from the viewpoint that it is easy for the resin composition to flow into the fine concavo-convex structure formed on the surface of a mold, it is preferable that the viscosity is not too high. Specifically, the viscosity of the resin composition measured at 25° C. using a rotary B type viscometer is preferably 10,000 mPa·s or less, more preferably 5,000 mPa·s or less, and even more preferably 2,000 mPa·s or less.

However, even in a case in which the viscosity of the resin composition exceeds 10,000 mPa·s, there is no particular problem as long as it is possible to decrease the viscosity by heating the resin composition in advance at the time of contact with the mold. In this case, the viscosity of the resin composition measured at 70° C. using a rotary B type viscometer is preferably 5,000 mPa·s or less, and more preferably 2,000 mPa·s or less.

The lower limit of the viscosity of the resin composition is not particularly limited; however, when the viscosity is 10 mPa·s or more, it is preferable because a laminated structure can be efficiently produced without wet spreading.

"Intermediate Layer"

The structure of the invention may have an intermediate layer between the substrate and the fine concavo-convex structure layer.

By providing an intermediate layer, functions such as increase in the pencil hardness of the structure, adhesiveness to the substrate, ultraviolet shielding properties, antistatic properties, adjustment of haze, coloration, and designability can be imparted. The intermediate layer may be a single layer, or may be composed of two or more layers. Furthermore, in a case in which the structure has an intermediate layer, when the intermediate layer is allowed to have a function of dispersing energy at the time of abrasion, scratch resistance is further improved, which is preferable.

The surface of the intermediate layer may be smooth, and may have a fine concavo-convex structure.

The material for forming the intermediate layer is not particularly limited as long as the material does not have any adverse influence on the effects of the invention; however, it is preferable that the material includes an active energy ray-curable resin composition. Regarding the polymerizable components included in the active energy ray-curable resin composition, for example, the same components as the polymerizable components described above as the material for forming the fine concavo-convex structure layer can be used. Also, the active energy ray-curable resin composition may include various binders, inorganic fine particles, organic fine particles, and additives.

According to an embodiment of the invention, it is preferable that the material for forming the intermediate layer includes an active energy ray-curable resin composition, and the active energy ray-curable resin composition includes at least one (meth)acrylate selected from the group consisting of an ester (meth)acrylate and a urethane (meth)acrylate.

Examples of the ester (meth)acrylate include pentaerythritol (tri)tetraacrylate, dipentaerythritol (penta)hexaacrylate, and polypentaerythritol polyacrylate.

Examples of the urethane (meth)acrylate include a reaction product between pentaerythritol (tri)tetraacrylate and hexamethylene diisocyanate, and a reaction product between (poly)pentaerythritol (poly)acrylate and hexamethylene diisocyanate.

"Other Layers"

According to an embodiment of the invention, the structure may have an adhesive layer. It is preferable that the adhesive layer is disposed on the surface of the side where the fine concavo-convex structure layer is not disposed. That is, the structure of the invention may have an adhesive layer, a substrate, and a fine concavo-convex structure layer laminated in this order.

"Indentation Modulus"

The indentation modulus of the structure according to the invention can be measured using, for example, a micro-indentation hardness tester. The indentation modulus obtainable herein is correlated to Young's modulus. An description on the correlation between the indentation modulus and Young's modulus is described in "Evaluation of material characteristic values by universal hardness test" published in "Zairyo Shikken Gijutsu (Materials Testing Technology)" (Vol. 43, No. 2, p. 148-152, issue of April, 1998), written by Cornelia Heermant and Dieter Dengel, translated by Katayama, Shigeo and Sato Shigeo.

Meanwhile, regarding the indentation modulus according to the invention, the value measured by the following method is to be used. That is, a transparent glass plate ("large-sized slide glass, product No.: S9112" manufactured by Matsunami Glass Industries, Ltd., 76 mm×52 mm in size) is adhered to the surface on the substrate side of the structure, with an optical tacky adhesive being interposed therebetween. Using this as a sample, the indentation modulus of the structure can be measured by indenting the face on the fine concavo-convex structure layer side of the sample with an indenter using a micro-indentation hardness tester (apparatus name: FISCHERSCOPE HM2000XYp, manufactured by Fischer Technology, Inc.). It is preferable to employ a Vickers indenter (tetrahedral diamond pyramid) as the indenter, and to perform the evaluation in a constant temperature chamber (temperature: 23° C., humidity: 50% RH). Regarding the evaluation program, measurement is carried out under the conditions that indenting is performed for 5 seconds at 1 mN/s, subsequently creeping is performed for 10 seconds at 5 mN, and then unloading is performed for 5 seconds at 1 mN/s, and the amount of indentation of the indenter is subjected to a sequential analysis using an analytic software (WIN-HCU, manufactured by Fischer Technology, Inc.). Thereby, the indentation modulus of each sample can be calculated.

The indentation modulus of the structure is 1 MPa to 1300 MPa, preferably 50 MPa to 500 MPa, and more preferably 160 MPa to 300 MPa. When the indentation modulus of the structure is 1 MPa or more, coalescence or disintegration of the protrusions having a size in the order of nanometers, which occurs when the material forming the fine concavo-convex structure layer is too soft, can be prevented. Furthermore, when the indentation modulus is 1300 MPa or less, the convexities of the fine concavo-convex structure layer can be prevented from becoming easily breakable against external pressure.

As such, in order to obtain a structure having an indentation modulus of 1 MPa to 1300 MPa, it is preferable to use an active energy ray-curable resin composition including the (meth)acrylate having an oxyethylene group described above, as the material that forms the fine concavo-convex structure layer.

"Coefficient of Kinetic Friction"

The coefficient of kinetic friction of the structure surface according to the invention can be calculated by reciprocally abrading the structure surface using a frictional abrasion tester. Specifically, a value measured according to the following method is to be used. That is, a transparent glass plate ("Large-sized slide glass, product No.: S9112" manufactured by Matsunami Glass Industries, Ltd., size: 76 mm×52 mm) is adhered to the surface on the substrate side of the structure, with an optical tacky adhesive being interposed therebetween. Using this as a sample, a reciprocating abrasion test of the sample is carried out using a frictional abrasion tester (apparatus name: TRIBOGEAR Type; HHS2000, manufactured by Shinto Scientific Co., Ltd.). The coefficient of kinetic friction can be calculated by attaching BEMCOT (manufactured by Asahi Kasei Fibers Corp., wiper for clean rooms, BEMCOT M-3II) to an indenter which measures 2 cm on each of four sides, and performing a 1000-reciprocating abrasion test under the conditions of a load of 1000 g, a stroke of 30 mm, and a speed of 30 mm/s.

In general, the abrasion phenomenon of a test specimen in a reciprocating abrasion test can be classified into the following three classes, depending on the change in the coefficient of kinetic friction in the relationship between the frequency of reciprocation and the coefficient of kinetic friction.

"Initial wear", in which the coefficient of kinetic friction increases or decreases at a constant rate "Normal wear", in which the coefficient of kinetic friction remains at an almost constant value "Abnormal wear", in which the coefficient of kinetic friction increases rapidly Here, when the rate of change in the coefficient of kinetic friction in the stage of initial wear in a reciprocating abrasion test is designated as $\Delta\mu s$, and the rate of change in the coefficient of kinetic friction immediately before the end of the test is designated as $\Delta\mu f$, the ratio thereof, $\Delta\mu$ ($\Delta\mu f/\Delta\mu s$), provides a value that reflects the extent of the progress of wear.

For example, in the case of $\Delta\mu \approx 1$, the stage of initial wear is maintained up to the end of the abrasion test, and this implies that the structure has excellent scratch resistance. On the other hand, in a case in which $\Delta\mu$ is smaller than 1, since the wear behavior undergoes a transition from initial wear to the stage of normal wear, the scratch resistance may be deteriorated compared to the case in which initial wear is maintained. Furthermore, in a case in which $\Delta\mu$ is larger than 1, this implies that wear progresses up to the stage of abnormal wear, and the surface of the structure has been significantly damaged.

By performing a reciprocating abrasion test, the surface state of the structure changes as follows.

In a state in which the concavities and convexities of the fine concavo-convex structure layer are retained without wearing down, the coefficient of kinetic friction increases or decreases at a constant rate. This state is referred to as the stage of initial wear. In regard to the reciprocating abrasion test, it is contemplated that as this stage of initial wear is longer, the structure has superior scratch resistance.

As the wearing of the convexities of the fine concavo-convex structure layer proceeds, the coefficient of kinetic friction remains at an almost constant value in the reciprocating abrasion test. This state is referred to as the stage of normal wear. As the wearing of the fine concavo-convex structure layer further proceeds, the coefficient of kinetic friction increases rapidly in the reciprocating abrasion test. This state is referred to as the stage of abnormal wear.

In the reciprocating abrasion test of a structure having a fine concavo-convex structure layer on the surface, since transition occurs from the stage of initial wear to the stage of normal wear and the stage of abnormal wear in sequence as described above, the rate of change in the coefficient of kinetic friction of the stage of initial wear can be determined by measuring the amount of change in the coefficient of kinetic friction from the initiation of the test to the $50^{th}$ back-and-forth movement. Specifically, a correlation diagram for the frequency of reciprocation of the reciprocal abrasion test and the coefficient of kinetic friction thus obtained is produced, a first order approximation is calculated for the value of the coefficient of kinetic friction of the stage of initial wear, and the gradient of this first order approximation is calculated. Thereby, the rate of change in the coefficient of kinetic friction of the stage of initial wear can be calculated.

The rate of change in the coefficient of kinetic friction of the stage of initial wear ($\Delta\mu s$) according to the present specification means the value obtained by producing a first order approximation for the curve of the coefficient of kinetic friction from the $20^{th}$ back-and-forth movement to the $40^{th}$ back-and-forth movement, and calculating the rate of change from the gradient of this first order approximation.

Similarly, the rate of change of the coefficient of kinetic friction immediately before the end of the test ($\Delta\mu f$) means the value obtained by producing a first order approximation for the curve of the coefficient of kinetic friction immediately before the end of the test, that is, from the $800^{th}$ back-and-forth movement to the $1000^{th}$ back-and-forth movement, and calculating the rate of change from the gradient of this first order approximation.

In regard to the structure of the invention, $\Delta\mu$, which is the ratio of the rates of change in the coefficient of kinetic friction, is 0.15 to 1.05, more preferably 0.3 to 1.0, and even more preferably 0.6 to 0.9. When $\Delta\mu$ is in the range of 0.15 to 1.05, the stage of initial wear is maintained for a long period, and thus a structure having excellent scratch resistance can be obtained.

Furthermore, the coefficient of kinetic friction in the early stage of test ($\mu s$) in an abrasion test is a value reflecting the slipperiness of the structure surface, and as the $\mu s$ value is smaller, the dirt adhering to the surface can be wiped off with a smaller load (force). Here, the coefficient of kinetic friction in the early stage of test refers to the coefficient of kinetic friction at the end of one back-and-forth movement in a reciprocating abrasion test for a structure surface. Furthermore, the coefficient of kinetic friction of a structure surface of the invention refers to the coefficient of kinetic friction in the early stage of test as described above.

In regard to the structure of the invention, $\mu s$ is preferably 0.55 or less, and more preferably 0.38 to 0.5. When $\mu s$ is 0.55 or less, the load (force) required to wipe off dirt becomes small, and the protrusions (convexities) having a size in the order of nanometers can be prevented from being damaged.

According to an embodiment of the invention, regarding a method of obtaining a structure having a $\Delta\mu$ of 0.1 to 1.05, as described above, it is preferable to use an active energy ray-curable resin composition including at least a (meth) acrylate having an oxyethylene group as the material that forms the fine concavo-convex structure layer. Furthermore, it is preferable to adjust the pitch of the convexities to 120 nm or more, and even more preferably to 140 nm or more.

Also, according to another embodiment of the invention, there is provided a method for detecting a structure having excellent scratch resistance.

That is, there is provided a method for detecting a structure provided with a fine concavo-convex structure layer having excellent scratch resistance, the method including a step of measuring the indentation modulus of the structure; a step of measuring the coefficient of kinetic friction of the structure surface; and a step of detecting a structure in which the indentation modulus is in the range of 1 MPa to 1300 MPa, and the ratio of the rates of change in the coefficient of kinetic friction ($\Delta\mu$) of the structure surface represented by the following Formula (1), is 0.15 to 1.05:

$$\Delta\mu = \Delta\mu f / \Delta\mu s \quad (1)$$

wherein in Formula (1), $\Delta\mu s$ represents the rate of change in the coefficient of kinetic friction in the stage of initial wear in the reciprocating abrasion test for the structure surface; and $\Delta\mu f$ represents the rate of change in the coefficient of kinetic friction immediately before the end of the test in the reciprocating abrasion test for the structure surface.

<Applications>

The structure of the invention can be optimally used as a functional article having a fine concavo-convex structure on the surface. Examples of the functional article include an antireflection article and a water-repellent article, both having the structure of the invention. Particularly, a display device or an automotive member, which includes the structure of the invention, is suitable as a functional article.

An antireflection article including the structure of the invention exhibits high scratch resistance and satisfactory antireflection performance. Examples of the antireflection article include articles produced by attaching the structure of the invention to the surfaces of objects such as various display devices such as an image display device (a liquid crystal display device, a plasma display panel, an electroluminescent display, a cathode ray tube display device, a fish finder display, a medical monitoring device, and the like), lenses, show windows, and color gauges.

The structure of the invention has excellent water-repellency due to the fine concavo-convex structure on the surface, and thus exhibits high scratch resistance and satisfactorily water repellency performance, while exhibiting excellent antireflection performance. Examples of a water-repellent article include articles produced by attaching the structure of the invention to the surfaces of objects such as window materials, roof tiles, pipes, outdoor lightings, convex traffic mirrors installed at road curves, windows for vehicles, mirrors for vehicles, inner lids for food products, tubes, beverage containers, and yogurt lids.

For each of the objects, when the part to be attached with the structure has a three-dimensional shape, a substrate having a shape corresponding to that shape may be prepared in advance, a surface layer may be formed on the substrate to obtain a structure, and then this structure may be attached to the predetermined part of the object.

Furthermore, in a case in which the object is an image display device, the structure of the invention may be attached not only to the surface, but also to the front face plate thereof, or the front face plate itself may also be constructed from the structure of the invention.

The structure of the invention can also be applied to, for example, optical applications such as an optical waveguide, a relief hologram, a lens, and a polarizing separation element; and applications such as a cell culture sheet, snow removing equipment, sports goods such as a ski plate and a snowboard, a heat storage material, a heat insulation material, a soundproofing material, fingerprint determination, and a ventilating fan.

<Method for Producing Structure>

In regard to the method for producing the structure of the invention, the method for forming a fine concavo-convex structure layer disposed on the surface is not particularly limited as long as the structure has the effects of the invention; however, the method is preferably a transfer method using a mold, specifically, a method of forming a fine concavo-convex structure layer by bringing the above-mentioned resin composition into contact with a mold having an inverse structure of the fine concavo-convex structure on the surface, and curing the resin composition (nanoimprint method). That is, the method for producing the structure of the invention preferably includes a step of forming a fine concavo-convex structure layer by a nanoimprint method.

Hereinafter, an example of the mold used for the transfer method will be described.

(Mold)

The mold has an inverse structure of the fine concavo-convex structure on the surface.

Examples of the material for the mold include metals (including metals having an oxide film formed on the surface), quartz, glass, resins, and ceramics.

Examples of the shape of the mold include a roll shape, a circular tube shape, a flat plate shape, and a sheet shape.

Examples of the method for producing a mold include method (I-1) and method (I-2) described below. Among them, from the viewpoint that large-sized screen production is enabled, and production is convenient, method (I-1) is preferred.

(I-1) A method of forming an inverse structure of the fine concavo-convex structure by a method of forming anodized alumina having plural pores (concavities) on the surface of an aluminum substrate.

(I-2) A method of forming an inverse structure of the fine concavo-convex structure by an electron beam lithography method, a laser light interference method or the like, on the surface of a mold substrate.

Regarding the method (I-1), a method including the following steps (a) to (f) is preferred.

(a) A step of anodizing an aluminum substrate in a liquid electrolyte at a constant voltage, and thereby forming an oxide film on the surface of the aluminum substrate.

(b) A step of removing a portion or the entirety of the oxide film, and forming pore generating points of anodization on the surface of the aluminum substrate.

(c) After step (b), a step of anodizing the aluminum substrate again in a liquid electrolyte, and forming an oxide film having pores at the pore generating points.

(d) After step (c), a step of expanding the diameters of the pores.

(e) After step (d), a step of anodizing the aluminum substrate again in a liquid electrolyte.

(f) A step of repeatedly performing step (d) and step (e), and obtaining a mold in which anodized alumina having plural pores is formed on the surface of an aluminum substrate.

Step (a):

As illustrated in FIG. 2, an oxide film 24 having pores 22 is formed by anodizing an aluminum substrate 20. Examples of the shape of the aluminum substrate include a roll shape, a circular tube shape, a flat plate shape, and a sheet shape.

Since there are occasions in which the grease used when an aluminum substrate is processed into a predetermined shape is adhering to the aluminum substrate, it is preferable that the aluminum substrate is subjected to a degreasing treatment in advance. Furthermore, it is preferable that the aluminum substrate is subjected to a polishing treatment in order to make the surface state smooth.

The purity of aluminum is preferably 99% or higher, more preferably 99.5% or higher, and even more preferably 99.8% or higher. If the purity of aluminum is low, when the aluminum substrate is anodized, a concavo-convex structure having a size which scatters visible light may be formed as a result of segregation of impurities, or the regularity of the pores obtainable by anodization may be decreased.

Examples of the liquid electrolyte include sulfuric acid, oxalic acid, and phosphoric acid.

In a case in which oxalic acid is used as a liquid electrolyte, the concentration of oxalic acid is preferably 0.8 M or less. When the concentration of oxalic acid is 0.8 M or less, an increase in the current value is prevented, and roughening of the surface of the oxide film can be suppressed.

Furthermore, when the formation voltage is 30 V to 100 V, anodized alumina having pores with high regularity with a period of 100 nm to 200 nm can be obtained. If the formation voltage is higher or lower than this range, the regularity tends to decrease. The temperature of the liquid electrolyte is preferably 60° C. or lower, and more preferably 45° C. or lower. When the temperature of the liquid electrolyte is 60° C. or lower, the occurrence of a phenomenon so-called "burning" can be prevented, and breakage of pores, or the pore regularity being disordered due to melting of the surface, can be suppressed.

In the case of using sulfuric acid as a liquid electrolyte, the concentration of sulfuric acid is preferably 0.7 M or less. When the concentration of sulfuric acid is 0.7 M or less, an increase in the current value is prevented, and a constant voltage can be maintained.

Furthermore, when the formation voltage is 25 V to 30 V, anodized alumina having pores with high regularity with a period of 63 nm can be obtained. If the formation voltage is higher or lower than this range, the regularity tends to decrease. The temperature of the liquid electrolyte is preferably 30° C. or lower, and more preferably 20° C. or lower. When the temperature of the liquid electrolyte is 30° C. or lower, the occurrence of a phenomenon so-called "burning" can be prevented, and breakage of pores, or the pore regularity being disordered due to melting of the surface, can be suppressed.

Step (b):

As illustrated in FIG. 2, the regularity of pores can be enhanced by first removing a portion or the entirety of the oxide film 24, and using this as the pore generating points 26 of anodization. Even in a state in which not the entirety of the oxide film 24 has been removed but a portion thereof remains, if there remains a portion of the oxide film 24 that can have sufficiently increased the regularity, the purpose of removing the oxide film can be accomplished.

Regarding the method of removing the oxide film 24, a method of removing the oxide film 24 by dissolving the oxide film 24 in a solution which does not dissolve aluminum but can selectively dissolve the oxide film 24, may be used. Examples of such a solution include a chromic acid/phosphoric acid mixed liquid.

Step (c):

As illustrated in FIG. 2, when the aluminum substrate 20 from which the oxide film has been removed is anodized again, an oxide film 24 having cylindrical pores 22 is formed.

The anodization can be carried out under the same conditions as those for step (a). As the time for anodization is made longer, deeper pores can be obtained.

Step (d):

As illustrated in FIG. 2, a treatment of expanding the diameter of the pores 22 (hereinafter, referred to as "pore diameter expanding treatment") is carried out. The pore diameter expanding treatment is a treatment of expanding the diameters of the pores obtained by anodization by immersing the aluminum substrate in a solution which can dissolve the oxide film 24. Examples of such a solution include an aqueous phosphoric acid solution having a concentration of about 5% by mass.

As the time for the pore diameter expanding treatment is made longer, the diameters of the pores become larger.

Step (e):

As illustrated in FIG. 2, when anodization is carried out again, cylindrical pores 22 having smaller diameters, which extend further downward from the bottom of the cylindrical pores 22, are further formed.

The anodization can be carried out under the same conditions as those for step (a). As the time for anodization is made longer, deeper pores can be obtained.

Step (f):

As illustrated in FIG. 2, by repeating the pore diameter expanding treatment of step (d) and the anodization of step (e), an oxide film 24 having pores 22 having a shape in which the diameter continuously decreases from the opening toward the depth direction, is formed. Thereby, a mold 28 having anodized alumina (porous oxide film of aluminum (alumite)) on the surface of an aluminum substrate 20 is obtained. It is preferable that the process finally ends in step (d).

The number of repetitions is preferably 3 or more times in total, and more preferably 5 or more times in total. When the number of repetitions is 3 or more times, the diameter of the pores continuously decrease, and a moth eye structure having a sufficient reflectance decreasing effect is obtained.

Examples of the shape of the pores 22 include an approximately conical shape, a pyramidal shape, and a cylindrical shape. A shape in which the cross-section of a pore in a direction perpendicular to the depth direction continuously decreases from the outermost surface toward the depth direction, such as a conical shape or a pyramidal shape, is preferred.

The average interval between adjoining pores 22 is preferably less than or equal to the wavelength of visible light, that is, 400 nm or less, more preferably 25 nm to 300 nm, and even more preferably 80 nm to 250 nm.

The average interval between adjoining pores 22 is a value obtained by measuring the interval between adjoining pores 22 (distance from the center of a pore 22 to the center of an adjacent pore 22) at 50 sites by electron microscopy, and averaging these values.

The average depth of the pores 22 is preferably 100 nm to 400 nm, and more preferably 130 nm to 300 nm.

The average depth of the pores 22 is a value obtained by measuring, at 50 sites, the distance between the bottommost part of a pore 22 and the apex of a convexity existing between the pores 22, which can be determined when a cross-sectional view diagram of the structure is observed at a magnification ratio of 30,000 times by the electron microscopic observation, and averaging these values.

The aspect ratio of the pores 22 (average depth of the pores 22/average interval between adjoining pores 22) is preferably 0.3 to 4, and more preferably 0.8 to 2.5.

The surface of the mold on the side where the fine concavo-convex structure has been formed may be treated with a mold releasing agent.

Examples of the mold releasing agent include a silicone resin, a fluorine resin, a fluorine compound, and a phosphoric acid ester, and a fluorine compound and a phosphoric acid ester are preferred.

Commercially available products of the fluorine compound include "FLUOROLINK" manufactured by Solvay Specialty Polymers Japan K.K.; fluoroalkylsilane "KBM-7803" manufactured by Shin-Etsu Chemical Co., Ltd.; "MRAF" manufactured by Asahi Glass Co., Ltd.; "OPTOOL HD1100" and "OPTOOL HD2100 series" manufactured by Harves Co., Ltd.; "OPTOOL DSX" manufactured by Daikin Industries, Ltd.; "NOVEC EGC-1720" manufactured by Sumitomo 3M, Ltd.; and "FS-2050" series manufactured by Fluoro Technology Co., Ltd.

The phosphoric acid ester is preferably a (poly)oxyalkylene alkyl phosphoric acid compound. Commercially available products include "JP-506H" manufactured by Johoku Chemical Co., Ltd.; "MOLDWIZ INT-1856" manufactured by Axel Plastics Research Laboratories, Inc.; and "TDP-10", "TDP-8", "TDP-6", "TDP-2", "DDP-10", "DDP-8", "DDP-6", "DDP-4", "DDP-2", "TLP-4", "TCP-5", and "DLP-10" manufactured by Nikko Chemicals Co., Ltd.

These mold releasing agents may be used singly, or in combination of two or more kinds thereof.

In a case in which a fine concavo-convex structure is formed by a transfer method using a mold obtainable as such, which has anodized alumina on the surface of an aluminum substrate, the fine concavo-convex structure of the structure is formed by transferring the fine concavo-convex structure of the surface of the anodized alumina.

In the following, an example of the production apparatus for producing the structure, and the method for producing the structure using the relevant production apparatus will be specifically described.

<Production Apparatus and Method for Producing Structure>

The structure 10 illustrated in FIG. 1 is produced as described below, for example, using the production apparatus illustrated in FIG. 3.

A material for forming a surface layer (active energy ray-curable resin composition) is supplied from a tank to the space between a roll-shaped mold 30 having an inverse structure of a fine concavo-convex structure (not shown in the diagram) on the surface and a substrate 12, which is a band-shaped film moving along the surface of the roll-shaped mold 30.

The substrate 12 and the material are nipped between the roll-shaped mold 30 and a nip roll 36 at which the nip pressure has been adjusted by a pneumatic cylinder 34. Thereby, the material is uniformly spread through between the substrate 12 and the roll-shaped mold 30, and also, the material is filled inside the concavities of the fine concavo-convex structure of the roll-shaped mold 30.

The material is cured by irradiating the material with active energy rays through the substrate 12 from an active energy ray irradiation apparatus 38 provided below the roll-shaped molding 30. Thereby, a structure 10 to which the fine concavo-convex structure on the surface of the roll-shaped mold 30 has been transferred as illustrated in FIG. 1, is obtained.

The active energy ray irradiation apparatus 38 is preferably a high pressure mercury lamp, a metal halide lamp, a LED lamp or the like. The amount of light irradiation energy is preferably 100 mJ/cm$^2$ to 10,000 mJ/cm$^2$.

<Operating Effect>

Since the structure 10 described above has a fine concavo-convex structure on the surface, the structure 10 has excellent antireflection performance.

Furthermore, a separating film may be provided on the back surface of the substrate of the structure 10, with a tacky adhesive material layer being interposed therebetween. By providing the tacky adhesive material layer, the structure 10 can be easily attached to another film-like or sheet-like article (front face plate, a polarizing element, or the like).

Other embodiments of the invention are as follows.

<1> A structure including a substrate; and a fine concavo-convex structure layer provided on at least one face of the substrate, the structure having the fine concavo-convex structure layer disposed on the surface of the structure, in which the indentation modulus is 1 MPa to 1300 MPa, and the ratio of the rates of change in the coefficient of kinetic friction (Δμ) of the structure surface represented by Formula (1) described above is 0.15 to 1.05, and fine concavo-convex structure layer is formed from a cured product of an active energy ray-curable resin composition including at least a (meth)acrylate having an oxyethylene group selected from the group consisting of polyethylene glycol diacrylate, an ethylene oxide adduct of dipentaerythritol hexaacrylate, and ethoxylated pentaerythritol tetraacrylate.

<2> The structure according to <1>, wherein the content of the (meth)acrylate having an oxyethylene group is 30 parts to 100 parts by mass relative to 100 parts by mass of the polymerizable components included in a cured product of the active energy ray-curable resin composition.

<3> The structure according to <1> or <2>, wherein the active energy ray-curable resin composition further includes a modified silicone resin.

<4> The structure according to any one of <1> to <3>, wherein the content of the modified silicone resin is 1 part to 13 parts by mass relative to 100 parts by mass of the polymerizable components.

<5> The structure according to any one of <1> to <4>, wherein the active energy ray-curable resin composition does not include urethane (meth)acrylate.

EXAMPLES

Hereinafter, the invention will be specifically described by way of Examples, but the invention is not intended to be limited to these.

(Preparation of Active Energy Ray-Curable Resin Composition A)

20 parts by mass of pentaerythritol triacrylate (manufactured by Dai-ichi Kogyo Seiyaku Co., Ltd., trade name: "NEW FRONTIER PET-3") and 80 parts by mass of ethoxylated pentaerythritol tetraacrylate (manufactured by Shin Nakamura Chemical Co., Ltd., trade name: "ATM-35E") as polymerizable components, 0.1 parts by mass of 1-hydroxycyclohexyl phenyl ketone (manufactured by Ciba-Geigy Japan, Ltd., trade name: IRGACURE 184") and 0.5 parts by mass of bis(2,4,6-trimethylbenzoyl)-phenylphosphine oxide (manufactured by Ciba-Geigy Japan, Ltd., trade name: "IRGACURE 819") as polymerization initiators, and 0.1 parts by mass of a mold releasing agent (manufactured by Nikko Chemicals Co., Ltd., trade name: "TDP-2") were mixed, and an active energy ray-curable resin composition A (resin composition A) was prepared.

(Preparation of Active Energy Ray-Curable Resin Compositions B to M)

Various active energy ray-curable resin compositions were prepared by the same operation as the case of the active energy ray-curable resin composition A, except that the composition was changed to the compositions described in Table 1.

TABLE 1

|  | Resin composition | PET-3 | ATM-35E | DPEA-12 | M-260 | BYK-3570 | DPHA | CN2271E | CN152 | APG200 | HEA | Polymerization initiator IRG.184 | IRG. 819 | Mold releasing agent TDP-2 |
|---|---|---|---|---|---|---|---|---|---|---|---|---|---|---|
| Example 1 | A | 20 | 80 |  |  |  |  |  |  |  |  | 0.1 | 0.5 | 0.1 |
| Example 2 | B |  |  | 50 | 50 |  |  |  |  |  |  | 0.1 | 0.5 | 0.1 |
| Example 3 | C |  |  | 70 | 30 |  |  |  |  |  |  | 0.1 | 0.5 | 0.1 |
| Example 4 | D | 20 |  |  | 80 |  |  |  |  |  |  | 0.1 | 0.5 | 0.1 |
| Example 5 | E | 20 |  |  | 79 | 1 |  |  |  |  |  | 0.1 | 0.5 | 0.1 |
| Example 6 | F | 19 |  |  | 76 | 5 |  |  |  |  |  | 0.1 | 0.5 | 0.1 |
| Example 7 | G | 18 |  |  | 73 | 9 |  |  |  |  |  | 0.1 | 0.5 | 0.1 |
| Example 8 | H | 17 |  |  | 70 | 13 |  |  |  |  |  | 0.1 | 0.5 | 0.1 |

TABLE 1-continued

| Resin composition | | PET-3 | ATM-35E | DPEA-12 | M-260 | BYK-3570 | DPHA | CN2271E | CN152 | APG200 | HEA | Polymerization initiator | | Mold releasing agent |
|---|---|---|---|---|---|---|---|---|---|---|---|---|---|---|
| | | | | | | | | | | | | IRG.184 | IRG.819 | TDP-2 |
| Comparative Example 1 | I | 25 | | 25 | 25 | 25 | | | | | | 0.1 | 0.5 | 0.1 |
| Comparative Example 2 | J | | 40 | | 50 | | | | | | 10 | 0.1 | 0.5 | 0.1 |
| Comparative Example 3 | K | | | | | | 80 | 20 | | | | 0.1 | 0.5 | 0.1 |
| Comparative Example 4 | L | | | | | | 30 | | 70 | | | 0.1 | 0.5 | 0.1 |
| Comparative Example 5 | M | | | | | | 15 | | 85 | | | 0.1 | 0.5 | 0.1 |

The components described in Table 1 are shown below.

"PET-3": Pentaerythritol triacrylate (manufactured by Dai-ichi Kogyo Seiyaku Co., Ltd., trade name: "NEW FRONTIER PET-3")

"ATM-35E": Ethoxylated pentaerythritol tetraacrylate (manufactured by Shin Nakamura Chemical Co., Ltd., trade name: "ATM-35E")

"DPEA-12": EO-modified compound of dipentaerythritol hexaacrylate (manufactured by Nippon Kayaku Co., Ltd., trade name: "DPEA-12")

"M-260": Polyethylene glycol diacrylate (manufactured by Toagosei Co., Ltd., trade name: "M-260")

"BYK-3570": Polyether-modified silicone oil (manufactured by BYK Chemie Japan K.K., trade name: "BYK-3570")

"DPHA": Dipentaerythritol hexaacrylate (manufactured by Nippon Kayaku Co., Ltd., trade name: "DPHA")

"CN2271E": Polyester acrylate oligomer (manufactured by Sartomer, LLC., trade name: "CN2271E")

"CN152": Epoxy acrylate oligomer (manufactured by Sartomer, LLC., trade name: "CN152")

"APG-200": Tripropylene glycol diacrylate (manufactured by Shin Nakamura Chemical Co., Ltd., trade name: "APG-200")

"HEA": 2-Hydroxyethyl acrylate (manufactured by Osaka Organic Chemical Industry, Ltd., trade name: "HEA")

"IRG. 184": 1-Hydroxycyclohexyl phenyl ketone (manufactured by BASF, trade name: "IRGACURE 184")

"IRG. 819": Bis(2,4,6-trimethylbenzoyl)-phenylphosphine oxide (manufactured by BASF, trade name: "IRGACURE 819")

"TDP-2": (manufactured by Nikko Chemicals Co., Ltd., trade name: "TDP-2")

<Measurement and Evaluation>

(Measurement of Pores of Mold)

A portion of a mold was cut out, and the surface and the vertical sections were vapor deposited with platinum for 1 minute. The mold was observed under magnification at 20,000 times at an accelerating voltage of 3.00 kV using a field emission type scanning electron microscope (manufactured by JEOL, Ltd., "JSM-7400F"), and the interval between adjoining pores (distance from the center of a pore to the center of an adjacent pore) was measured at 50 sites. The average value of the measured values was designated as the average interval of adjoining pores.

Furthermore, the vertical sections of the mold were observed under magnification at 20,000 times, and the distance between the bottommost part of a pore and the apex of a convexity existing between pores was measured at 50 sites was measured at 50 sites. Thus, the average value of the measured values was designated as the average depth of the pores.

(Measurement of Convexities of Fine Concavo-Convex Structure)

The surface layer and vertical sections of a measurement sample were vapor deposited with platinum for 10 minutes, and the measurement sample was observed under magnification at 20,000 times at an accelerating voltage of 3.00 kV using a field emission type scanning electron microscope (manufactured by JEOL, Ltd., "JSM-7400F"). Thus, the interval between adjoining convexities (distance from the center of a convexity to the center of an adjacent convexity) was measured at 50 sites, and the average value of the measured values was designated as the average interval between adjoining convexities.

Furthermore, sections of the measurement sample were observed under magnification at 20,000 times, and the distance between the bottommost part of a convexity and the apex of a concavity existing between convexities was measured at 50 sites. The average value of the measured values was designated as the average height.

(Reciprocating Abrasion Test)

A transparent glass plate (manufactured by Matsunami Glass Industries, Ltd., "Large-sized slide glass, product No.: S9112", size: 76 mm×52 mm) was attached to the surface on the substrate side of a structure, with an optical tacky adhesive interposed therebetween, and this was used as a sample. A reciprocating abrasion test of the sample was carried out using a frictional abrasion tester (apparatus name: TRIBOGEAR Type: HHS2000, manufactured by Shinto Scientific Co., Ltd.). BEMCOT (wiper for clean rooms, manufactured by Asahi Kasei Fibers Corp., BEMCOT M-3II) was attached to an indenter that measured 2 cm on each of four sides, and a 1000-reciprocating abrasion test was carried out under the conditions of a load of 1000 g, a stroke of 30 mm, and a speed of 30 mm/s. Thus, the coefficient of kinetic friction was calculated.

Meanwhile, the coefficient of kinetic friction at the time of completion of one back-and-forth movement was designated as Ls.

(Scratch Resistance)

For the sample after the reciprocating abrasion test, the face of the glass plate on the side that the structure was not attached was painted black, and the scratch state of the structure surface was visually evaluated.

S: No scratch is recognized.

A: There are fewer than 5 recognizable scratches, and the site of abrasion is not clouded in white.

B: There are 5 or more and fewer than 20 recognizable scratches, and the site of abrasion is slightly clouded in white.

C: There are 20 or more recognizable scratches, and the site of abrasion clearly appears to be clouded in white.

D: The surface layer has been scraped off, and scratches reaches to the substrate.

(Calculation of Δμ from Abrasion Progress Curve)

Figure 4:
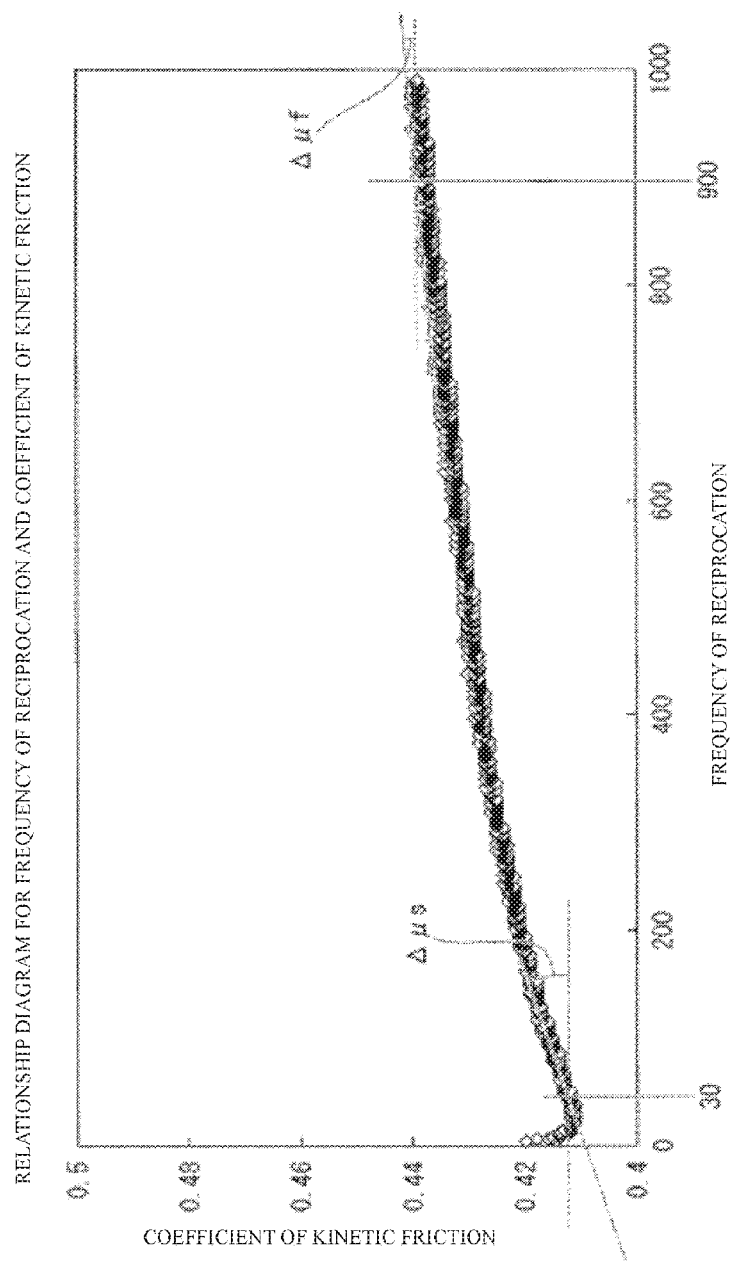
FIG. 4 is an exemplary diagram showing the relationship between the frequency of reciprocation and the coefficient of kinetic friction, which is obtainable from the results of a reciprocating abrasion test.

As illustrated in FIG. 4, a relationship diagram between the frequency of reciprocation and the coefficient of kinetic friction was produced from the results of the reciprocating abrasion test, the tangent line of the curve at the time of the end of 30 back-and-forth movements was determined, and the value of the gradient was designated as Δμs. The tangent line was defined as a straight line obtained by approximating the curve over the range including before and after 10 back-and-forth movements (20 to 40 back-and-forth movements) by a linear expression.

Furthermore, the tangent line of the curve at the time of completion of 900 back-and-forth movements was determined in the same manner, and the value of the gradient was designated as Δμf. The tangent line was defined as a straight line obtained by approximating the curve over the range including before and after 100 back-and-forth movements (800 to 1000 back-and-forth movements) by a linear expression.

From the values obtained as described above, Δμ (Δμf/Δμs) was calculated.

(Measurement of Indentation Modulus)

A transparent glass plate (manufactured by Matsunami Glass Industries, Ltd., "Large-sized slide glass, product No.: S9112", size: 76 mm×52 mm) was attached to the surface on the substrate side of the structure, with an optical tacky adhesive interposed therebetween, and this was used as a sample. The indentation modulus of the sample was measured using a micro-indentation hardness tester (apparatus name: FISCHERSCOPE HM2000XYp, manufactured by Fischer Technology, Inc.). For the indenter, a Vickers indenter (tetrahedral diamond pyramid) was employed, and the evaluation was carried out in a constant temperature chamber (temperature: 23° C., humidity: 50%). Regarding the evaluation program, the measurement was carried out under the conditions that indenting was performed for 5 seconds at 1 mN/s, subsequently creeping was performed for 10 seconds at 5 mN, and then unloading was performed for 5 seconds at 1 mN/s, and the indentation moduli of various samples were calculated using an analytic software (WIN-HCU, manufactured by Fischer Technology, Inc.).

"Production of Mold Having Inverse Structure of Fine Concavo-Convex Structure"

An aluminum plate having a purity of 99.99% by mass and a thickness of 0.3 mm was cut out into a size of 30 mm×90 mm, and the aluminum plate was subjected to electrolytic polishing in perchloric acid/ethanol mixed liquid (volume ratio=1/4). The resultant was used as an aluminum substrate.

Step (a):

4.6 L of a 0.05 M aqueous oxalic acid solution was used as a liquid electrolyte, and while the liquid electrolyte was stirred at 350 rpm with a half-moon-shaped stirring blade having a diameter of 8 cm and a height of 2 cm, the initial temperature of the liquid electrolyte was adjusted to 15° C. The aluminum substrate was immersed in the liquid electrolyte and was anodized for 5 minutes at an applied voltage of 80 V. Thus, an oxide film was formed.

Step (b):

The aluminum substrate having an oxide film formed thereon was immersed for 3 hours in an aqueous solution at 70° C. produced by mixing 6% by mass of phosphoric acid and 1.8% by mass of chromic acid, and the oxide film was removed by dissolution. Thus, pits that served as the pore generating points of anodization were exposed.

Step (c):

The aluminum substrate with exposed pore generating points was immersed in a 0.05 M aqueous oxalic acid solution that was adjusted to 15° C., and was anodized for 6 seconds at 80 V. Thus, an oxide film was formed again on the surface of the aluminum substrate.

Step (d):

The aluminum substrate having an oxide film formed thereon was immersed for 19 minutes in a 5 mass % aqueous phosphoric acid solution that was adjusted to 32° C., and was subjected to a pore diameter expanding treatment of expanding the pores of the oxide film.

Step (e):

The step (c) described above and the step (e) described above were further repeated alternately for 4 times, and step (d) was carried out at the end. That is, step (c) was carried out 5 times in total, and step (d) was carried out 5 times in total.

Thereafter, the aluminum substrate was washed with deionized water, and then the moisture of the surface was removed by air blowing. Thus, a mold on which an oxide film having approximately conical-shaped pores with an average interval of 180 nm and an average depth of about 160 nm was formed, was obtained.

The mold obtained in this manner was immersed for 10 minutes in an aqueous solution obtained by diluting TDP-8 (manufactured by Nikko Chemicals Co., Ltd.) to 0.1% by mass, and was air dried overnight. Thereby, a release-treated mold was obtained.

Example 1

Several droplets of the resin composition A were dropped on the surface of the mold. A triacetyl cellulose film (manufactured by Fujifilm Corp., "TD80ULM"; hereinafter, also referred to as "TAC film") having a thickness of 80 μm was used as a substrate, and while the resin composition A on the mold was spread out with the substrate, the substrate was coated with the resin composition A. Thereafter, the resin composition A was cured by irradiating the resin composition A with ultraviolet radiation with energy of 1000 mJ/cm$^2$ using a high pressure mercury lamp through the substrate side. A cured product of the resin composition A was released from the mold for each substrate, and thereby, a structure having a fine concavo-convex structure on the surface of a substrate, with an average interval between adjoining convexities of 180 nm and an average height of convexities of 150 nm (aspect ratio: 0.83), was obtained.

For the structure thus obtained, a reciprocating abrasion test and the analysis of the indentation modulus were carried out. The evaluation results are presented in Table 2.

Examples 2 to 8 and Comparative Examples 1 to 5

Structures were produced by the same operation as in Example 1, except that the resin composition A was changed to the resin compositions described in Table 1, and various analyses and evaluations were carried out. The results are presented in Table 2.

TABLE 2

| | Indentation modulus (MPa) | Scratch resistance | Coefficient of kinetic friction (μs) | Δμs | Δμf | Δμ |
|---|---|---|---|---|---|---|
| Example 1 | 200 | S | 0.44 | $2.7 \times 10^{-5}$ | $1.8 \times 10^{-5}$ | 0.67 |
| Example 2 | 252 | A | 0.48 | $1.1 \times 10^{-3}$ | $3.5 \times 10^{-4}$ | 0.32 |
| Example 3 | 450 | B | 0.48 | $2.4 \times 10^{-4}$ | $3.8 \times 10^{-5}$ | 0.16 |
| Example 4 | 200 | B | 0.48 | $1.1 \times 10^{-3}$ | $3.1 \times 10^{-4}$ | 0.27 |
| Example 5 | 188 | B | 0.50 | $1.2 \times 10^{-3}$ | $2.2 \times 10^{-4}$ | 0.19 |
| Example 6 | 178 | S | 0.44 | $3.0 \times 10^{-4}$ | $2.6 \times 10^{-4}$ | 0.86 |
| Example 7 | 167 | A | 0.38 | $5.1 \times 10^{-4}$ | $2.5 \times 10^{-4}$ | 0.50 |
| Example 8 | 150 | B | 0.43 | $7.0 \times 10^{-4}$ | $2.3 \times 10^{-4}$ | 0.33 |
| Comparative Example 1 | 1990 | C | 0.50 | $6.0 \times 10^{-4}$ | $5.9 \times 10^{-5}$ | 0.10 |
| Comparative Example 2 | 1470 | D | 0.39 | $1.8 \times 10^{-3}$ | $1.1 \times 10^{-4}$ | 0.06 |
| Comparative Example 3 | 29 | D | 0.64 | $1.4 \times 10^{-3}$ | 0.0 | 0.00 |
| Comparative Example 4 | 188 | C | 0.35 | $6.5 \times 10^{-4}$ | $7.0 \times 10^{-5}$ | 0.11 |
| Comparative Example 5 | 535 | C | 0.31 | $3.8 \times 10^{-4}$ | $4.4 \times 10^{-5}$ | 0.11 |

As is obvious from the results of Table 2, the structures of Examples 1 and 6 exhibited especially excellent scratch resistance because the indentation modulus of the surface layer was appropriately controlled, and the stage of initial wear was still maintained even at the time of completion of the reciprocating abrasion test.

The structures of Examples 2 and 7 exhibited excellent scratch resistance because the indentation modulus of the surface layer was appropriately controlled, and the state of initial wear was maintained for a relatively long time in the reciprocating abrasion test.

The structures of Examples 3 to 5 and 8 had the indentation modulus of the surface layer appropriately controlled, and the structures were in a state in which normal wear was slightly in progress at the time of completion of the reciprocating abrasion test. Thus, the structures exhibited satisfactory scratch resistance.

On the other hand, regarding the structure of Comparative Example 1, since the indentation modulus of the surface layer was higher than 1300 MPa, the protrusions having a size in the order of nanometers (convexities of the fine concavo-convex structure layer) were easily bent against a load. Also, since normal wear had progressed at the time of completion of the reciprocating abrasion test, the rate of results for visually evaluating the structure surface after the reciprocating abrasion test was C.

Regarding the structure of Comparative Example 2, since the indentation modulus of the surface layer was higher than 1300 MPa, the protrusions having a size in the order of nanometers were easily bent against a load. Also, the stage of initial wear in the reciprocating abrasion test was short, and the scratch resistance was insufficient. Thus, the rate of results for visually evaluating the structure surface after the reciprocating abrasion test was D.

Regarding the structure of Comparative Example 3, the rate of change in the coefficient of kinetic friction (Δμs) for the stage of initial wear in the reciprocating abrasion test was high. Also, the coefficient of friction increased significantly along with the progress of initial wear, and the coefficient of friction exceeded the performance limit of the apparatus after more or less 500 back-and-forth movements, so that the coefficient of friction became not measurable. The rate of result for visually evaluating the structure surface at the time point at which the coefficient of friction became not measurable, was D.

Regarding the structures of Comparative Examples 4 and 5, the indentation moduli of the surface layer were appropriately controlled; however, the state of initial wear in the reciprocating abrasion test was short, and the scratch resistance was insufficient. Thus, the rate of results for visually evaluating the sample surface after the reciprocating abrasion test was C.

It was found from these results that according to the invention, when the indentation modulus of the surface layer is controlled, and when the increase in the coefficient of kinetic friction at the time of performing a reciprocating abrasion test for a surface having the fine concavo-convex structure described above is adjusted to an appropriate range, a structure having excellent scratch resistance without impairing the optical performance such as the antireflection performance is obtained.

INDUSTRIAL APPLICABILITY

The laminate structure of the invention is useful as an optical article, particularly an antireflection article such as an antireflection film, having excellent optical performance and excellent mechanical characteristics.

EXPLANATIONS OF LETTERS OR NUMERALS

10 Structure
12 Substrate
14 Surface layer
20 Aluminum substrate
22 Pore
24 Oxide film
26 Pore generating point
28 Mold
30 Roll-shaped mold
32 Tank
34 Pneumatic cylinder
36 Nip roll
38 Active energy ray irradiation apparatus
40 Peeling roll

The invention claimed is:

1. A structure comprising a substrate and a fine concavo-convex structure layer provided on at least one face of the substrate,
   the fine concavo-convex structure layer being disposed on the surface of the structure and having an indentation modulus of 1 MPa to 1300 MPa and a ratio of the rates of change (Δμ) in the coefficient of kinetic friction of the surface of the structure represented by the following Formula (1), of 0.15 to 1.05:

$$\Delta\mu = \Delta\mu f / \Delta\mu s \quad (1)$$

wherein in Formula (1), Δμs represents the rate of change in the coefficient of kinetic friction in the stage of initial wear in a reciprocating abrasion test of the fine concavo-convex structure layer surface; and Δμf represents the rate of change in the coefficient of kinetic friction immediately before the end of the test in the reciprocating abrasion test.

2. The structure according to claim 1, wherein the average interval between adjoining convexities in the fine concavo-convex structure layer is 400 nm or less, and the aspect ratio of the convexities is 0.7 to 1.4.

3. The structure according to claim 1, wherein the average interval between adjoining convexities of the fine concavo-convex structure layer is 120 nm to 250 nm.

4. The structure according to claim 1, wherein the fine concavo-convex structure layer contains a cured product of an active energy ray-curable resin composition, and the active energy ray-curable resin composition includes at least a (meth)acrylate having an oxyethylene group.

5. The structure according to claim 1, wherein the ratio of the rates of change in the coefficient of kinetic friction of the fine concavo-convex structure layer surface represented by Formula (1) is 0.3 to 1.0.

6. The structure according to claim 1, wherein the ratio of the rates of change in the coefficient of kinetic friction of the fine concavo-convex structure layer surface represented by Formula (1) is 0.6 to 0.9.

7. The structure according to claim 1, wherein the coefficient of kinetic friction of the fine concavo-convex structure layer surface is 0.55 or less.

8. The structure according to claim 1, wherein the coefficient of kinetic friction of the fine concavo-convex structure layer surface is 0.38 to 0.5.

9. The structure according to claim 1, wherein the indentation modulus of the fine concavo-convex structure layer is 160 MPa to 300 MPa.

10. The structure according to claim 1, further comprising an intermediate layer between the substrate and the fine concavo-convex structure layer.

11. The structure according to claim 10, wherein the intermediate layer contains a cured product of an active energy ray-curable resin composition, and the active energy ray-curable resin composition includes at least one (meth)acrylate selected from the group consisting of an ester (meth)acrylate and a urethane (meth)acrylate.

12. The structure according to claim 1, wherein the substrate is a light-transmitting substrate.

13. An article comprising the structure according to claim 1.

14. A method for producing the structure according to claim 1, the method comprising a step of forming a fine concavo-convex structure layer by a nanoimprint method.

* * * * *